(12) United States Patent
Llinas et al.

(10) Patent No.: US 8,583,261 B2
(45) Date of Patent: Nov. 12, 2013

(54) COCHLEAR IMPLANT WITH IMPROVED ELECTRODE ARRAY AND CONTROLLER

(75) Inventors: Rodolfo R. Llinas, New York, NY (US); Hirobumi Watanabe, New York, NY (US); Mutsuyuki Sugimori, New York, NY (US); Masayuki Nakao, Chiba-ken (JP)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/585,615

(22) Filed: Aug. 14, 2012

(65) Prior Publication Data
US 2012/0310258 A1 Dec. 6, 2012

Related U.S. Application Data

(62) Division of application No. 12/607,949, filed on Oct. 28, 2009, now Pat. No. 8,260,437.

(51) Int. Cl.
*A61N 1/05* (2006.01)

(52) U.S. Cl.
USPC .............................. 607/137; 607/55

(58) Field of Classification Search
USPC ................ 607/54–55, 137; 600/376
See application file for complete search history.

*Primary Examiner* — Carl H Layno
*Assistant Examiner* — Paula J Stice
(74) *Attorney, Agent, or Firm* — Foley & Lardner LLP (57) ABSTRACT

A cochlear implant device includes a deformable and stretchable flexible strip composed of a biological compatible material and positioned about a longitudinal axis so as to form a spiral. The implant device has a plurality of conductive strips with electrode windows formed so as to expose a segment of each conductive strip. A density of the electrode windows is sufficient to monitor a distance of the flexible strip from a non-conductive tissue of a patient in a 360 degree field of view about the longitudinal axis. A method of inserting a cochlear implant includes providing a multi-joint robot comprised of a series of actuator units, guiding the multi-joint robot into an inner ear of a patient, monitoring the position of the multi-joint robot relative to a non-conductive portion of the patient; and applying current to the multi-joint robot so as to adjust the position of the actuator units.

29 Claims, 11 Drawing Sheets

COCHLEAR IMPLANT WITH IMPROVED ELECTRODE ARRAY AND CONTROLLER

CROSS-REFERENCE TO RELATED PATENT APPLICATIONS

This divisional application claims priority to U.S. patent application Ser. No. 12/607,949, filed Oct. 28, 2009, now U.S. Pat. No. 8,260,437 and is incorporated herein by reference in its entirety.

FIELD OF THE INVENTION

The present invention relates generally to a cochlear implant, and more particularly to a cochlear implant with an increased array of electrodes so as to achieve a finer frequency resolution.

BACKGROUND OF THE INVENTION

The cochlea of the human ear contains hair cells that are essential to the perception of sound. These hair cells are found along substantially the full length of the spiral path followed by the cochlea. Sound vibrations distort certain structures of the cochlea which in turn distort the hair cells. It is believed that such distortion initiates electrical impulses in the hair cells. These impulses are conveyed to the fibers of the auditory nerve and ultimately to the brain.

Some instances of human hearing loss are attributed to extensive destruction of the hair cells. When this occurs, though the structures of the cochlea may otherwise be substantially intact, and the auditory nerve may be partially or completely intact, the auditory response is significantly impaired or non-existent.

To solve this problem, implants have been developed that can directly stimulate the auditory nerve in an individual with such hearing damage. These implanted hearing devices are designed to produce useful hearing sensations to persons with severe to profound nerve deafness by electrically stimulating nerves inside the inner ear. In the past 20 years cochlear implants have helped thousands of people with hearing impairments. In fact, recent research at the University of Michigan estimates that approximately 100,000 people worldwide have received cochlear implants.

In a traditional cochlear implant system, a microphone acquires sound from the environment. The sound is then selectively filtered by a speech processor, using various filter bank strategies such as Fast Fourier Transforms, to divide the signal into different frequency bands. Once processed, the signal is then sent to a transmitter, a coil held in position by a magnet placed behind the external ear. This transmitter sends the processed signal to the internal device by electromagnetic induction. Embedded in the skull, behind the ear is a receiver which converts the signal into electric impulses and sends them through an internal cable to electrodes. Conventional cochlear implants are made of multiple platinum electrodes or similar conductive material, connected to platinum wire and embedded in a silicone body. These electrodes then act to stimulate the auditory nerve fibers by generating an electric field when the electrical current is routed to them.

There are several shortcomings to the conventional implant. First, its operation is very different from the natural hearing mechanism of the ear. For example, the conventional electrode assembly cannot stimulate auditory nerve fibers throughout the full length of the basilar membrane. In effect, because a finite number of electrodes are involved, stimulation is limited to a certain number of points. In conventional cochlear implants, the function of 1,000 inner hair cells and 30,000 auditory neurons is instead generated with only 12 to 22 channels. Thus, the full frequency spectrum of human perceptible audio is coarsely reconstructed using 12-22 frequency bands. This accounts for reported limitations regarding sound frequencies that a user of the implant can perceive.

Another significant disadvantage of the conventional cochlear implant is that the installation of the cochlear implant can damage cochlear structures. During initial insertion, for example, the basilar membrane may be injured. Furthermore, additional damage may result inside the cochlea when the endolymph is perturbed. The resulting damage to the cochlear structure, including the basilar membrane, may make replacement of the implant, or substitution of an improved implant that may be developed in the future, difficult, if not impossible, and may cause permanent loss of residual hearing.

Short (10 mm) hybrid cochlear implants may be placed in the high frequency domain of the cochlea in patients with residual hearing in the low frequency range. Obviously, this strategy cannot be used in a patient with normal hearing in the high frequency range, having poor or no hearing of low frequency sounds. For these patients, a long cochlear implant that does not damage the basilar membrane is needed to completely preserve residual hearing while stimulating that part of the cochlea that encodes high frequency sounds.

Conventional techniques such as intra-operative and post-hoc imaging using low resolution computer tomography are insufficient to prevent damage to the basilar membrane during insertion.

Further, missing from the art is a cochlear implant having an array of electrodes that achieve a finer frequency resolution across a wider band. Also missing from the art is a system and method for implanting the cochlear implant without causing injury to the basilar membrane.

SUMMARY OF THE INVENTION

In one aspect, the invention provides a cochlear implant device that includes a deformable and stretchable flexible strip composed of a biological compatible material. The implant device has a plurality of conductive strips arranged in a predetermined pattern embedded within. A plurality of electrode windows is formed on one surface of the implant device so as to expose a segment of each conductive strip. The implant device is positioned about a longitudinal axis so as to form a spiral; and a density of the electrode windows provided along the deformable and stretchable flexible strip is sufficient to monitor a distance of the flexible strip from a non-conductive tissue of a patient in a 360 degree field of view about the longitudinal axis.

In another aspect, the invention provides a method of inserting a cochlear implant. The method includes providing a multi-joint robot comprised of a series of actuator units, placing the deformable and stretchable flexible strip about the outer surface of the multi-joint robot, guiding the multi-joint robot into an inner ear of a patient, monitoring the position of the multi-joint robot relative to a non-conductive portion of the patient; and applying current to the multi-joint robot so as to adjust one of the yaw and pitch position of one or more of the actuator units.

In yet another aspect, the invention provides a multi-joint robot for guiding an implant; the multi-joint robot includes a plurality of multi-joint actuator units interconnected mechanically and controllable electronically. Each of the plurality of multi-joint actuator units includes at least two central discs, an inner column disposed between the central discs, and at least three connecting wires interconnecting the central discs. The multi-joint actuator units are capable of independent remote activation by electronic communication.

These and other aspects, features, steps and advantages can be further appreciated from the accompanying figures and description of certain illustrative embodiments.

DETAILED DESCRIPTION OF ILLUSTRATIVE EMBODIMENTS

By way of overview and introduction, embodiments of the invention address the spiral ganglion cells with more electrodes to achieve a finer frequency resolution. To achieve this finer signal, a large number of electrodes are desirable. Accordingly, embodiments of the invention are directed to a spiral strip cochlear implant, which can have hundreds of electrodes located on the outside surface. Using microlithography as a fabrication method for 2D patterning, microlithography-based micro electrode arrays are able to provide the cochlear implant with more electrodes than in conventional methods. However, because microlithography is a fabrication method for 2D patterning, additional methods such as rolling or wrapping are necessary to build a 3D tubular structure that will fit the cochlear duct. Combining hundreds of electrodes and an optimized electrode configuration, a cochlear implant embodying the invention can pass more finely tuned current to auditory nerves for a greater frequency resolution. Furthermore, by using this method, the shape of the cochlear implant and the active electrodes can be tuned for each patient.

The insertion of conventional cochlear implants often damages the basilar membrane and perturbs the endolymph. A process embodying the present invention uses scanning electrochemical microscopy to guide the cochlear implant through the cochlea. Conventionally, scanning electrochemical microscopy is used to study the surface reactivity of materials at microscopic levels. Among several modes of scanning electrochemical microscopy, the negative mode can be used to sense the distance between an electrode tip and a nonconductive material. Moreover, the sensitivity of this probe is several times as long as the electrode size itself.

Used in the negative mode, scanning electrochemical microscopy continuously applies a constant voltage to pass current through a microelectrode in a conductive solution. This current is carried by the ions in the solution. The magnitude of the current is directly proportional to the ion diffusion in the solution. Accordingly, as the electrode approaches a non-conductive material, the faradic current decreases because ion diffusion decreases. This decrease can be detected by an electrochemical microscope. By recording the tip-current for a multitude of tip positions in a two dimensional direction, a three-dimensional image of the nonconductive surface can be acquired. Using scanning electrochemical microscopy techniques allows for the positioning of the cochlear implant in the inner ear without damage.

In another embodiment, a robotic cochlear implant device guides the cochlear implant through the cochlea. The robotic implant device includes position sensors to indicate in vivo the precise location of the cochlear implant on the order of microns. The hundreds of distance sensors are spirally distributed on, or near, the surface of the cochlear implant and equip the robotic implant device with a high number of sensors in order to acquire the complete positional relationship between the robotic implant device, which has many degree of freedom, and the tapered spiral cochlear duct.

Figure 1:
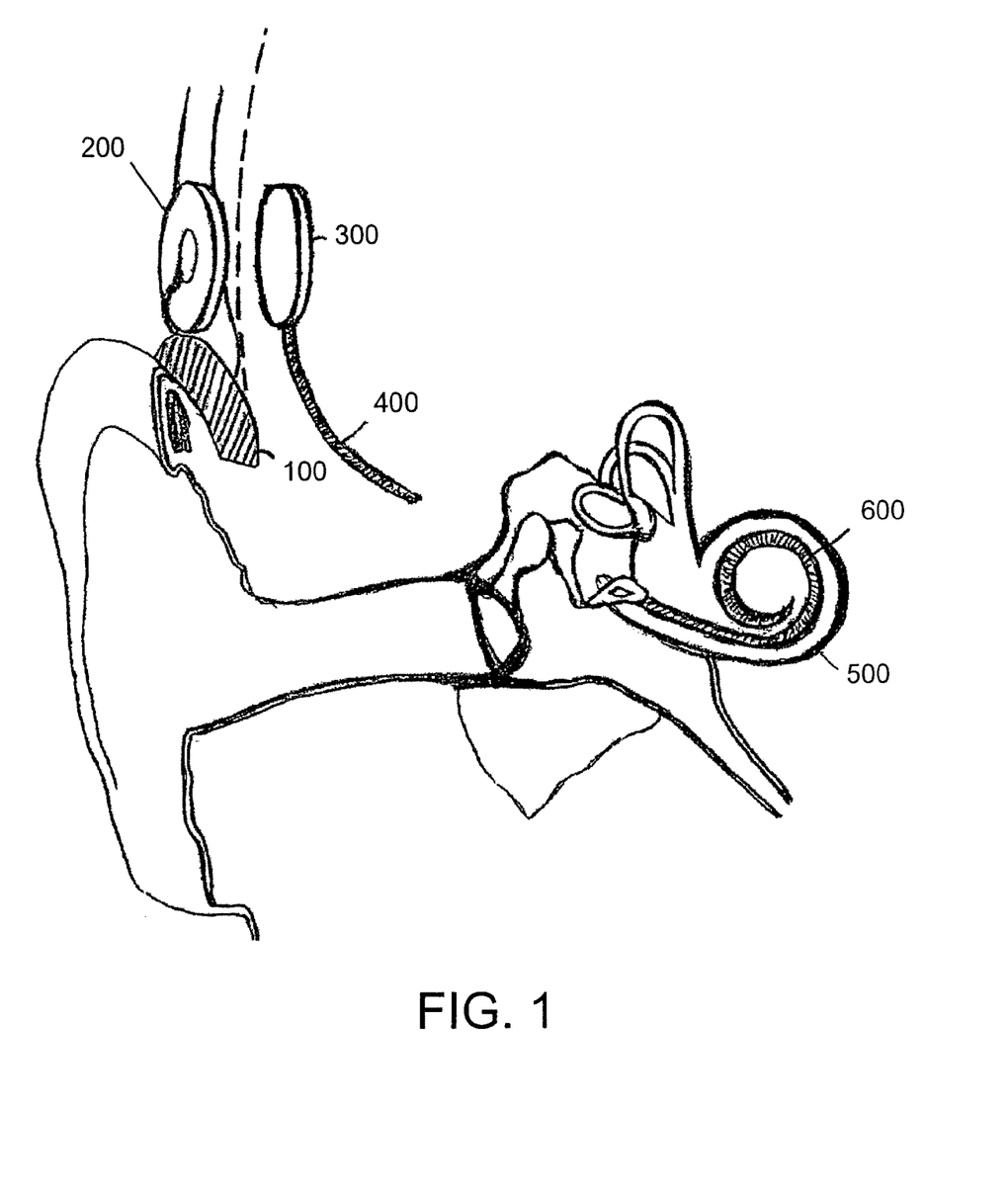
FIG. 1 is an illustration of a cochlear implant in accordance with an embodiment of the present invention.

The cochlear implant, represented in FIG. 1, may contain a microphone 100, which acquires sound from the environment. The sound may be selectively filtered by a speech processor, for example, by using various filter bank strategies such as Fast Fourier Transforms, to divide the signal into different frequency bands. Once processed, the signal may then be sent to a transmitter 200, for example, a coil held in position by a magnet placed behind the external ear. This transmitter may send the processed signal to an internal device, for example, by electromagnetic induction. Embedded in the skull, preferably behind the ear, is a receiver 300, which converts the signal into electric impulses and sends them, preferably through an internal cable 400, to electrodes included in an implant 600 inside the cochlea 500. The cochlear implants may be made of multiple platinum or gold electrodes or similar conductive material, which is preferably connected to platinum or gold wire and embedded in a silicone body. These electrodes may then act to stimulate the auditory nerve fibers by generating an electric field when the electrical current is routed to them.

Figure 2:
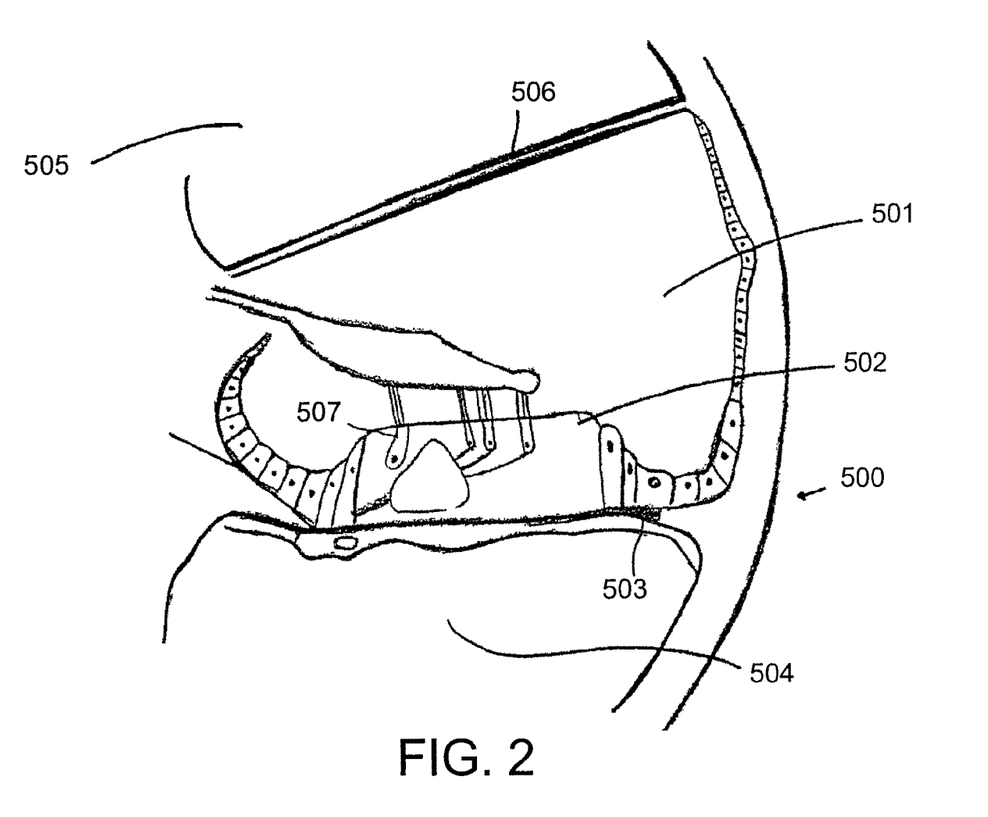
FIG. 2 is a schematic representation of the cross-section of the cochlea and particularly the location of the scala tympani.

FIG. 2 is a schematic representation of the cross-section of the cochlea 500. There are a multiple of typical types of injuries that occur during insertion of a conventional cochlear implant. The cochlea 500 is actually a system of three fluid filled tubes, helically coiled side by side, thus resembling a snail shell. The three tubes are known as the scala media 501, the scala vestibuli 505, and the scala tympani 504. The scala vestibuli 505 and the scala media 501 are separated from each other by a first membrane, known as Reissner's membrane 506, and the scala tympani 504 and scala media 501 are separated from each other by second membrane known as the basilar membrane 503. At the distal end of the cochlea, the scala vestibuli and the scala tympani are joined together such that a fluid called endolymph, which is present within both the scala vestibuli 505 and the scala tympani 504, can freely flow from one tube to the other. The basilar membrane 503 supports a structure known as the Organ of Corti 502 which contains a series of hair cells 507.

In a functioning ear, acoustic vibrations cause a flow of the endolymph within the scala vestibuli 505. This movement is in turn transmitted through the scala tympani 504 and eventually results in a vibration of the basilar membrane 503. While the exact mechanism is not yet certain, most researchers believe that this basilar membrane vibration causes a movement in the cilia, generating a change in the electrical potential across the outer membrane of the hair cell 507. This change in electrical potential causes a release of neurotransmitters. Upon release, the neurotransmitters trigger an action potential, which is propagated until it reaches the brain. As noted earlier, the insertion of a cochlear implant often damages the basilar membrane 503 and perturbs the endolymph, thus, causing further permanent damage to cochlear structures.

Figure 3:
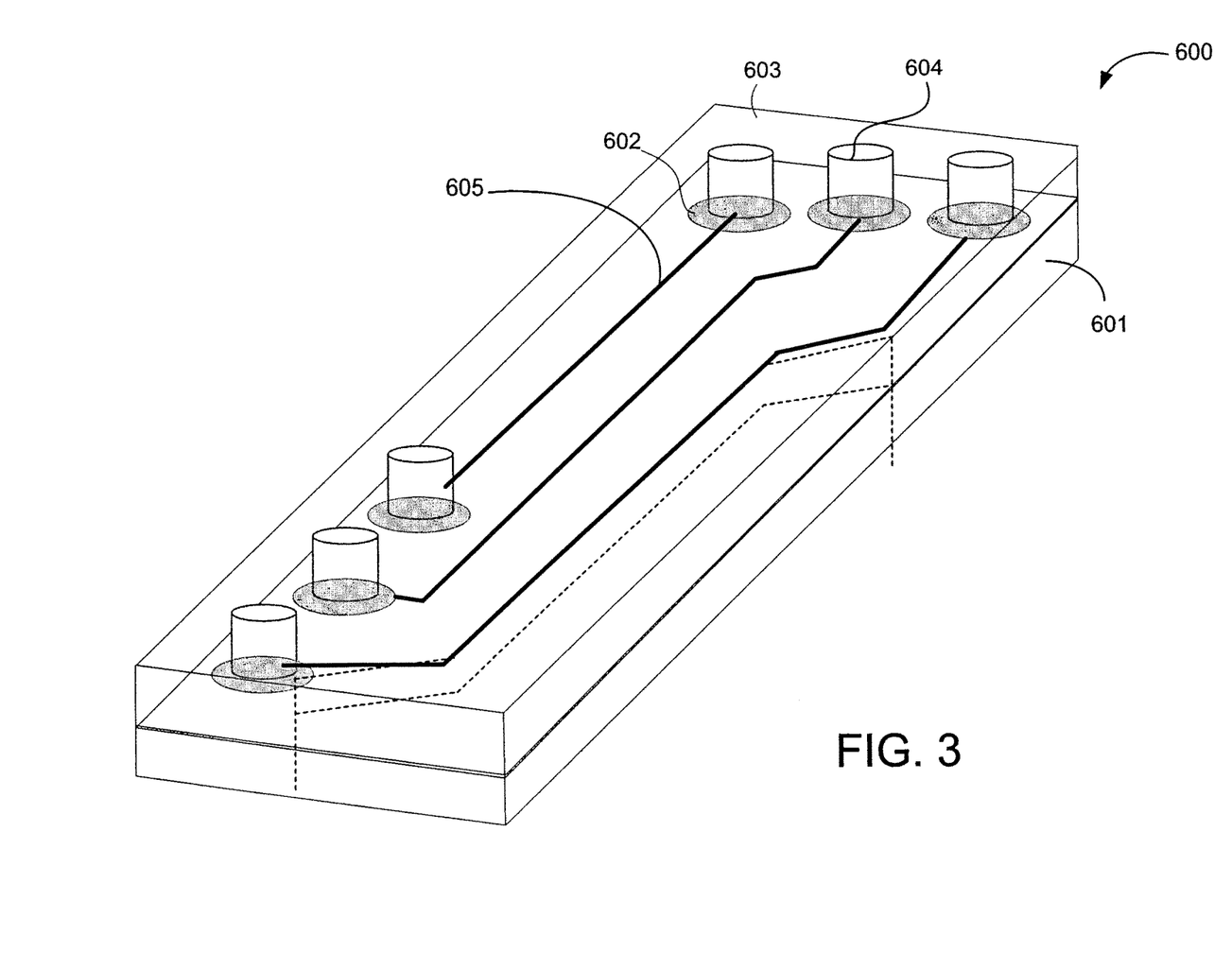
FIG. 3 shows an example of a spiral strip cochlear implant in accordance with an embodiment of the present invention before wrapping.

FIG. 3 illustrates a spiral strip cochlear implant 600 embodying the present invention. To manufacture the spiral strip cochlear implant 600, initially, a spin-on mold release layer (not shown) may be formed. The mold-release layer is used to hold silicone in place during fabrication of the spiral strip cochlear implant 600. A silicone layer 601 is applied to the mold release layer, preferably, by spin coating. Spin coating is a process used to apply a uniform thin film to a flat substrate by placing an amount of a solution on the substrate and then rotating the substrate at a high speed in order to spread the fluid evenly across the substrate. Electrode patterns may then be created on the silicone layer through a process of metal deposition and microlithography. The use of microlithography allows for a high flexibility in the design of electrode patterns. The electrode patterns create individual conductive strips 605. These conductive strips 605 can have pads 602 disposed at one or both ends. Optionally, pads 602 can be formed at several locations along the conductive strips 605. Upon completion of the microlithography, a second silicone layer 603 may be applied, for example by spin coating, and electrode windows 604 may then be created by the removal of the second layer material in discrete positions to form holes in the second layer of material, for example through microlithography. The holes may be placed above the ends of the conductive strips 605, and also may be placed above any intermediate pads 602 located along the conductive strips 605. Finally, the mold release layer may be removed. Holes may also be created in the first layer of silicone to provide access to the conductive strips 605. The resulting structure is a deformable and stretchable flexible strip that has an upper and lower surface. Within the structure are contained a multitude of conductive strips 605. The deformable and stretchable flexible strip itself may be formed from a suitable biological compatible material that is not rejected by a patient's immune system. Combining hundreds of electrodes and an optimized electrode configuration, the cochlear implant embodying the present invention can pass more finely tuned current to auditory nerves for a finer signal.

In one embodiment, photo patternable Polydimethylsiloxane (PDMS), which is a silicon-based organic polymer, available from Dow Corning may be used to fabricate the cochlear implant. PDMS is useful in biological applications such as cell culture studies and neural prosthesis. Furthermore, PDMS is elastic, with a max elongation of 37.6%, and flexible, with a Young's modulus of 160 MPa, making it an excellent candidate as it is both stretchable and deformable. However, the invention is not so limited, and other suitable materials for biological compatible applications other than PDMS are within its scope.

The silicone may be spun onto the mold release layer, e.g., a glass plate, preferably followed by UV exposure, and baking. Furthermore, the silicone may also be treated with plasma ashing to remove photo resist and enhance its affinity for chromium. Chromium can then be deposited on the silicone with plasma sputter followed by vapor deposition of gold. The deposition of gold is preferred as it is an excellent conductor that is also capable of tolerating deformation. The gold can be patterned with negative resist (e.g., AZ-150, AZ Electronics Materials) and masks. Upon development of the photoresist, gold can be etched in solution (e.g., $I_2$ 10 ml, KI 5 g and $H_2O$ 40 ml). The surfaces of patterned gold and silicone may then be cleaned with ethanol and distilled $H_2O$, followed by plasma ashing. Using the photopatternable silicone, the patterned gold can be coated except for the electrode windows 604 and connection pads. The silicone electrode on a glass substrate may then be cut with a femto-second laser and immersed in ethanol to dissolve the mold release layer and detach the silicone strip.

Figure 4:
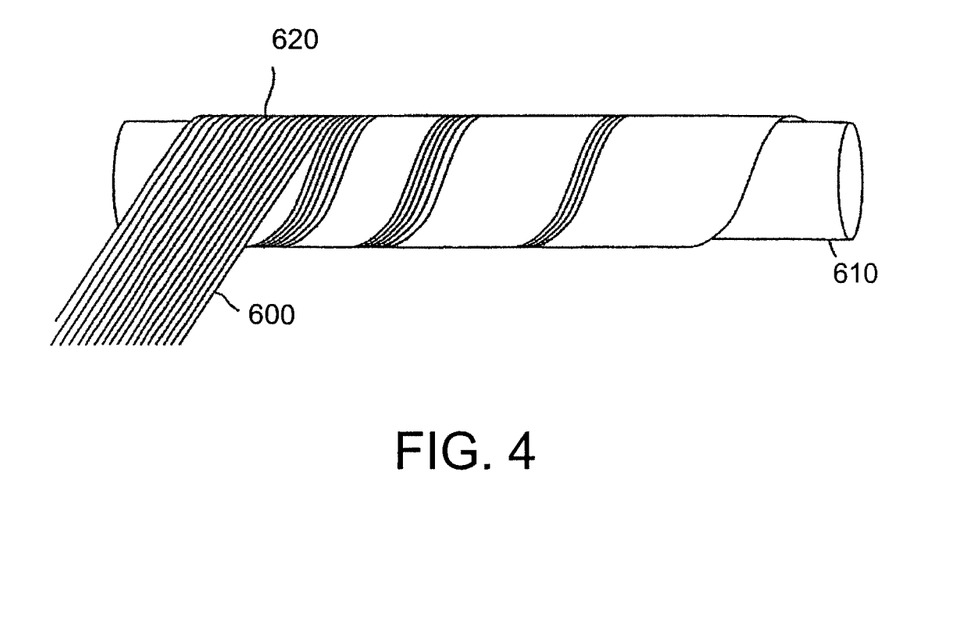
FIG. 4 shows wrapping the embodiment of FIG. 3 around a tube in order to create a shape suitable for implanting through the cochlear duct.

As can be appreciated from FIG. 4, the spiral strip cochlear implant 600 may then be rolled or wrapped around a tubular structure, such as a polyimide tube 610 in order to create the necessary three-dimensional shape for insertion into the cochlea. The result is a flexible spiral strip cochlear implant with electrodes 620 disposed on the outside surface depending on the desired pattern through microlithography. The desired mask pattern in conjunction with the quantity of electrode windows 604 provided along the length of the conductive strip 605 creates a density of electrode windows that permits the electrochemical microscopy scanning to sense the relative position of the spiral strip cochlear implant 600 to the surrounding non-conductive tissue. The density of electrodes can be greater than 10 within a 10% longitudinal segment of the spirally formed strip. This spiral strip cochlear implant 600 can be conformally shaped so as to be positioned safely within the scala tympani.

In one embodiment, the spiral strip cochlear implant is a cylinder 21 mm in length and 300 microns in diameter. The strip may have 300 electrode windows resulting in 70 microns between electrode windows longitudinally. The strip may be wrapped to make a helical shape whose pitch angle is 60°, resulting in a helix pitch of 560 microns. Thus, the distance between two electrode windows that are directed in the same direction is equal to the pitch of the helix (e.g. 560 microns). Within each turn of the helix among 40 such turns in a whole cochlear implant, there are 8 equally spaced electrode windows.

In one embodiment, 114 of the electrode windows are configured for stimulating spiral ganglion to elicit audition. Of these 114 electrode windows, 38 may be disposed closest to the inner wall of cochlear duct. Furthermore, each of the 38 electrode windows may be supported by two adjacent electrode windows. Thus, 76 additional electrode windows are disposed on the strip, which are rotated 45° away from the angle of the closest electrode windows. All 300 electrode windows, including the 114 stimulating electrode windows, may be used for scanning electrochemical microscopy-based position sensing as will be described in greater detail below.

The spiral strip cochlear implant may be implanted as part of a robotic cochlear implant, designed to achieve not only automatic continuous shape optimization along cochlear implant insertion but also configured for superior spiral ganglion electrical stimulation. As used hereinafter, the words "robot" and "robotic" may refer to a sensor unit, a processor, an actuator units or any combination used for positioning the cochlear implant. The robotic cochlear implant may include position sensors and a multi-joint robot 800. Additionally, an insertion device, such as a linear micromanipulator, may be used to feed the robotic cochlear implant longitudinally into a cochlear duct. A processor may also be used to monitor the position sensors, the multi-joint robot 800, and the linear micromanipulator in order to control the multi-joint robot 800 and the linear micromanipulator.

A processor may determine the incremental actuation of the implant as dependent on the shape of the cochlear duct, and the shape and the relative position of the cochlear implant. The shape of the cochlear duct may be determined by the longitudinal shape, and relative position of the cochlear implant. The relative position may be determined by the relative distance between the cochlear implant and the wall of cochlear duct from sensor information as will be described in greater detail below with reference to FIG. 5. Additionally, the longitudinal distance may be determined by previous insertion history, and the shape determined by historical position of actuation. After completion of longitudinal advancement, the cochlear implant may cause electrode windows to contact the wall of cochlear duct in order to stimulate the auditory nerve with maximum efficacy.

Figure 5:
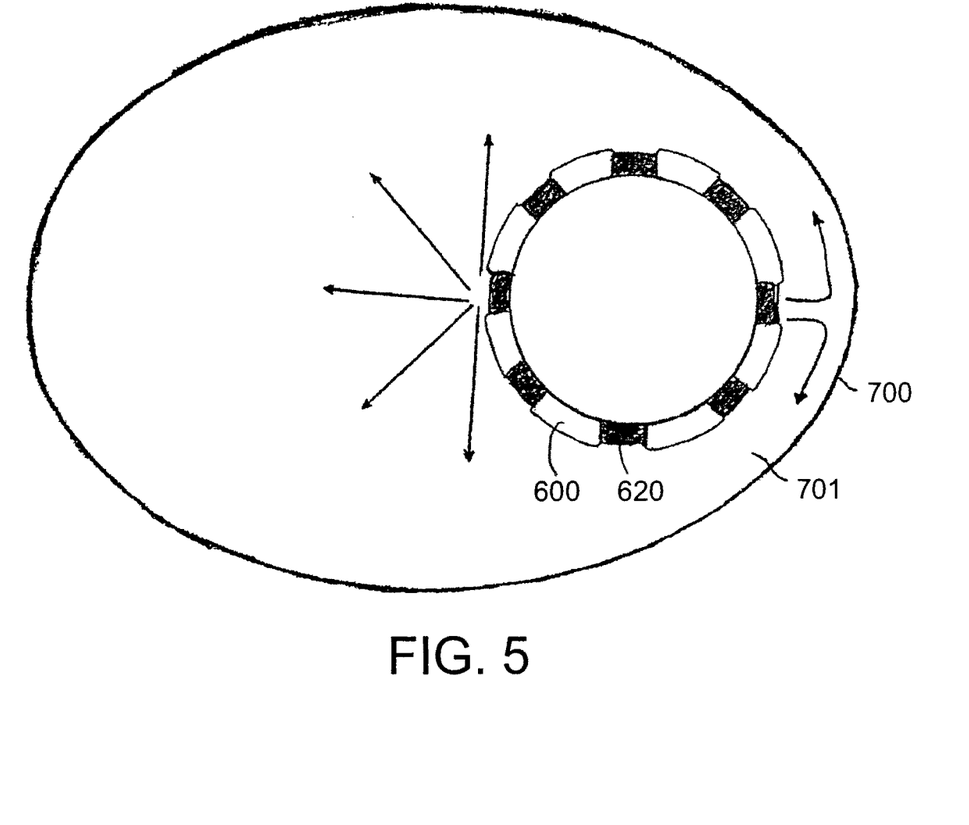
FIG. 5 is a schematic representation of using scanning electrochemical microscopy to guide the cochlear implant through the cochlea.

FIG. 5 is a schematic representation of using scanning electrochemical microscopy to guide the cochlear implant through the cochlea. To detect the position of the cochlear implant 600 relative to the wall of scala tympani 700, the same cochlear implant stimulation electrodes 620 are used as distance sensors by applying scanning electrochemical microscopy. The electrode windows have a suitable size for distance sensitivity and are aligned spirally along the robotic implant device so that they will sense the shape of the scala tympani wall 700 in the bony labyrinth. During implantation, the cochlear implant 600 may be surrounded by conductive material 701. Using scanning electrochemical microscopy in negative mode, the distance between the electrode window and the scala tympani wall can be measured, because the wall of the scala tympani 700 is made of non-conductive bone. Specifically when the electrodes sense that ion diffusion is small, e.g., is less than a predetermined threshold, and that impedance is large, e.g., is greater than a predetermined threshold, it will be recognized that the wall of the scala tympani 700 is near. Thus, the position of the cochlear implant can be determined relative to the scala tympani wall 700 and injury can be avoided.

The diameter of the scala tympani duct ranges from a few hundred microns to sub millimeters. Furthermore, the 40×40 micron electrode windows on the robotic implant device can sense non-conductive material such as the scala tympani wall 700 from a distance of up to about 200 microns. Therefore, when a 300 micron robotic implant device is inserted into the scala tympani region, which is less than 700 microns in diameter, the sensors can detect the wall continuously. Furthermore, a microlithographic pattern can be used to easily make smaller electrode windows for more sensitive distance sensing, or create any pattern thought to be advantageous in position determination.

As described above, the configuration of electrode windows is designed to achieve both the direction and the longitudinal resolution required for avoiding cochlear implant contact with the wall of cochlear duct. In one embodiment, the cross section of the implant includes electrode windows that are positioned 45° apart. In a strip having a pitch angle of 60°, the distance between adjacent electrode windows is 560 microns and the electrode windows provide sufficient resolution for position sensing to control actuator movement.

Figure 6:
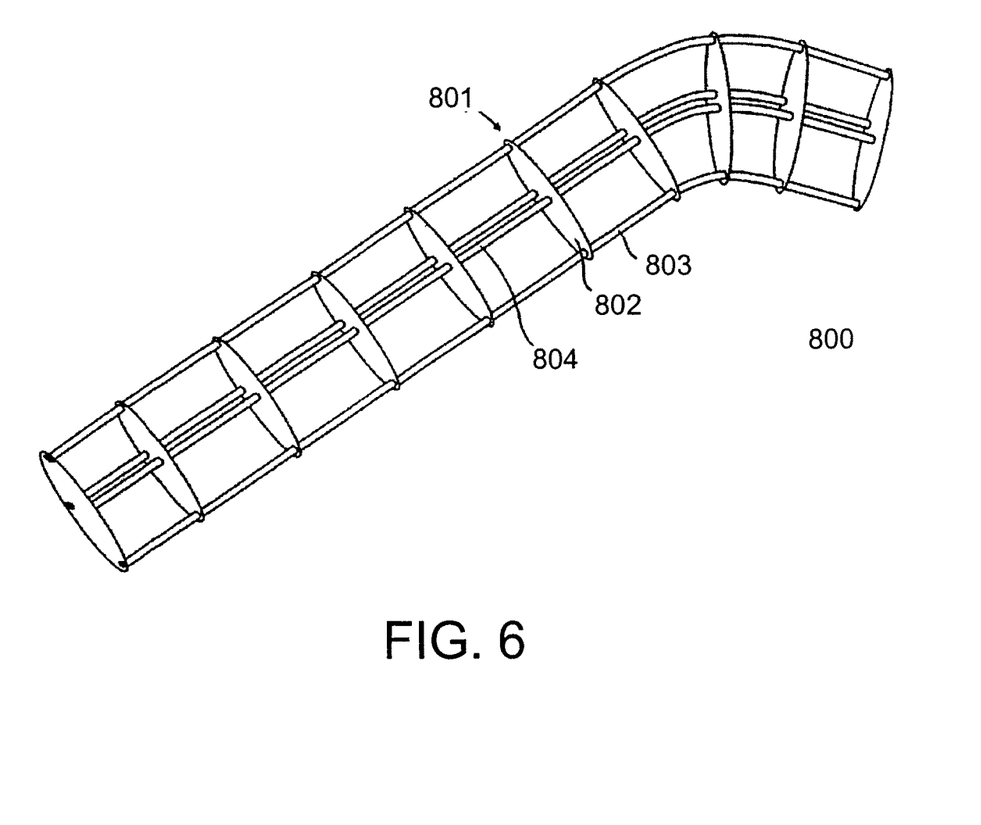
FIG. 6 is a diagrammatic representation of the micro multi-joint actuators.

FIG. 6 illustrates a multi-joint robot 800 in accordance with an embodiment of the invention. The multi-joint robot 800 may be useful in avoiding contact between the cochlear implant and the wall of the cochlear duct. The multi-joint robot 800 may be formed from a series of micro multi-joint actuator units 801. Overall, the multi-joint robot 800 may be 20 mm long with a 200 micron diameter. The multi-joint robot 800 may contain 100 micro multi-joint actuator units 801. Each actuator unit 801 is small and can be independently activated. Alternatively, activator units 801 may be combined into functional segments that are controlled as a group.

Figure 7:
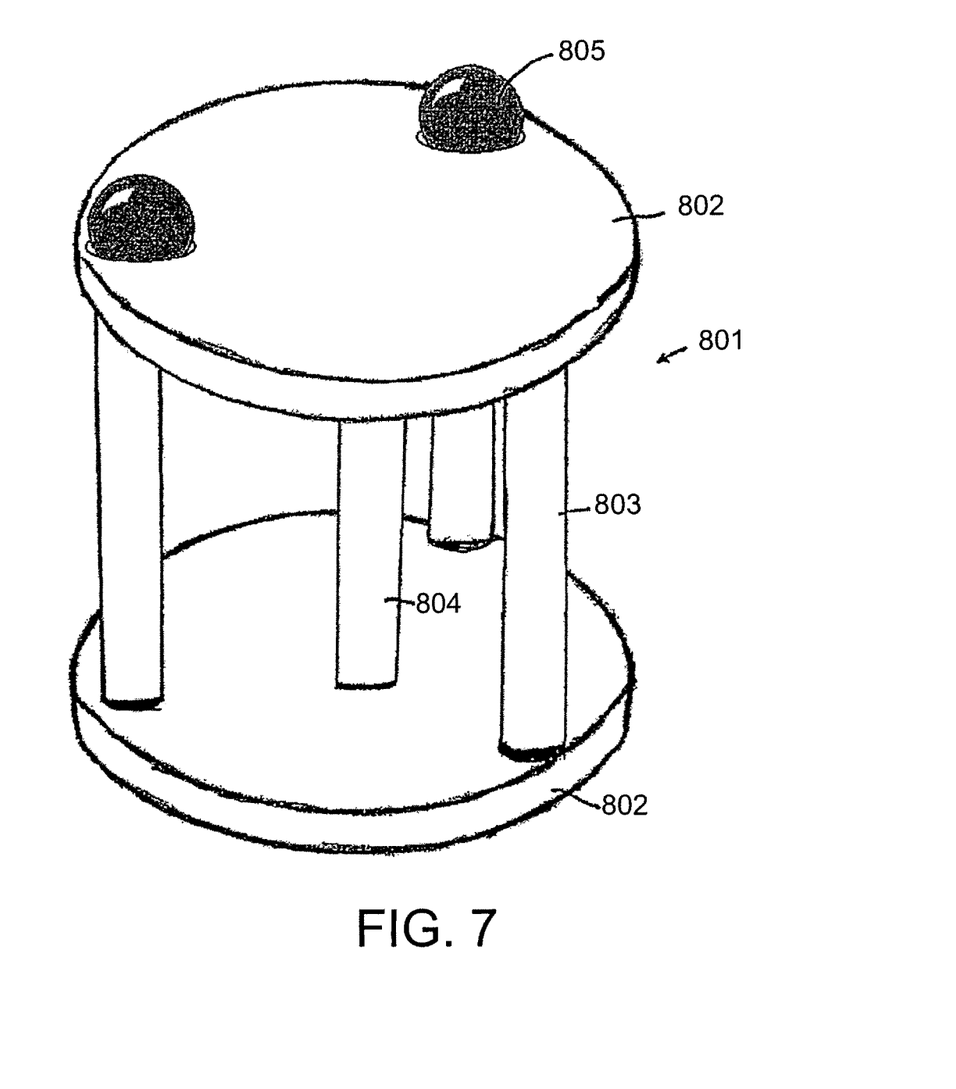
FIG. 7 is a diagrammatic representation of a single actuating unit of the micro multi-joint actuators.

As can be appreciated from FIG. 7, each joint actuator unit 801 may have three rigid components: two micro-tilt stages 802, an inner column 804, and three connecting wires 803 on the periphery. In one embodiment, the joint actuator unit 801 may be formed of two insulated tungsten 200 micron diameter, 10 micron thick discs connected with a 20 micron diameter, and 180 micron height tungsten column in the center of the two disks. The two disks may further be connected with three shape memory alloy wires, such as 25 micron diameter nickel-titanium (nitinol) wires (e.g., Flexinol®, Dynalloy, Inc.) distributed preferably at three equiangular points on the circumference of a 180 micron circle.

In one embodiment, the micro multi-joint actuator units 801 may be produced in the following manner: Using a femtosecond laser, the stages 802 are processed to have three 30 um holes for three shape memory alloy wires and a single 10 um hole for a center column. The stages may be insulated and the end of the center column may be sharpened by electropolishing. The three wires may then be assembled with the two stages 802. Preferably, the ends of the wires stick out of the stages 802 by approximately 10 um. These ends may be exposed with a YAG laser to form a spherical shape 805. The center column is then inserted between the two stages. The three wires may be slightly heated to pull on the two stages 802, which push the center column and keep the two stages 802 parallel.

Individual actuator units 801 may then be assembled into a functional segment. The two stages 802 and the spherically shaped wire ends 805 may be insulated, for example, with resin except for the tips of the wire ends. Two actuator units 801 may be connected, preferably glued, so as to electrically connect the wire ends of the first unit to the wire ends of the second unit. The ends of the columns of the two stages may similarly be electrically connected to form a common electrical ground connection between the actuator units 801. This process may then be repeated to create up to 10 or more units in a functional segment. Each end of a functional segment may be insulated so as to leave an electrical contact point of the wire ends 805 at the periphery of the outermost stages 802, to thereby allow conductive strips 605 in the spiral strip cochlear implant 600 to be electrically connected to the wire ends 805 when the spiral strip cochlear implant 600 is wrapped around the multi-joint robot 800. Alternatively, only one end of the functional segment may provide an electrical contact point to the wire ends 805; on the other end of the functional segment, the ends of the three wires may be connected to a common electrical ground connection formed by the electrically connected center columns. In this case, an electrical connection from the center columns to the periphery of one of the stages 802 may be included.

The functional segments may be glued to each other to form a complete multi-joint robot 800. The multi-joint robot 800 may be wrapped with the spiral strip cochlear implant 600 such that the wire ends 805 in the outermost actuator units 801 of each functional segment have electrical contact with conductive strips 605 in the spiral strip cochlear implant 600. Thus, each of the multi-joint actuator units 801 in a functional segment may be controlled by three conductive strips included in the spiral strip cochlear implant 600. Alternatively, each multi-joint actuator unit 801 may have independent connections to the spiral strip cochlear implant 600, thereby allowing for independent control of each multi-joint actuator unit 801.

Figure 8:
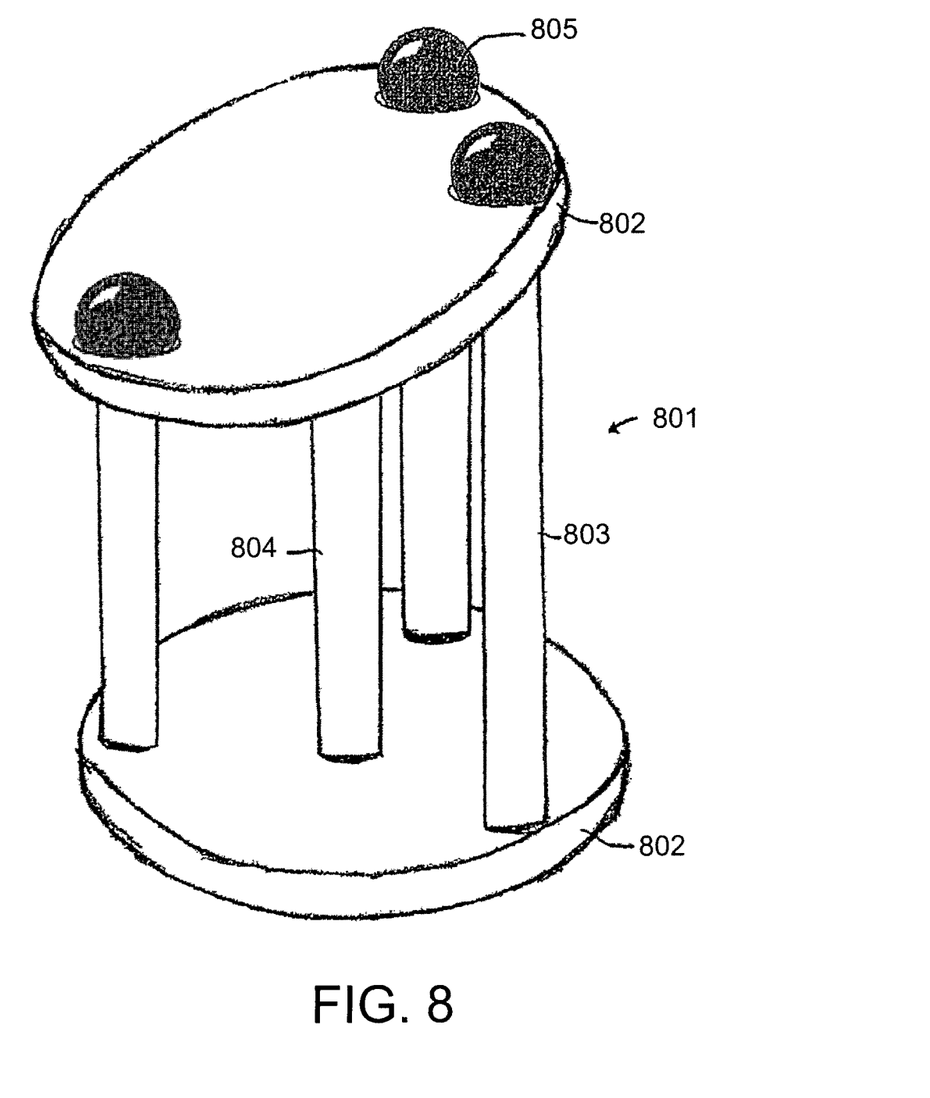
FIG. 8 is a diagrammatic representation of a single actuating unit of the micro multi-joint actuators in the left tilt position.

Thus, the actuator units 801 are fashioned in a manner such that applying electrical current to one or two of the shape memory alloy, e.g., nickel-titanium, wires in each functional segment will heat the wires and cause the wires to contract, thereby tilting each micro multi-joint actuator unit 801 in the functional segment in two-dimensions: yaw and pitch. Thus, by applying electrical current to the wires on the periphery of the micro-tilt stages 802, each actuator unit 801 in a functional segment may tilt in a right, left, forward, or back position. When the electrical current is no longer applied to the wires, the wires will cool and will retain the shape acquired while being heated by the electrical current. Furthermore, by monitoring the impedance of each of the series of wires connected together in each functional segment, the length of the series of wires may be determined and the tilt of each functional segment or actuator unit 801 may be precisely controlled. FIG. 8 shows a micro multi-joint actuator unit 801 in the left tilt position. Current may be applied selectively to each of the functional segments until the functional segment reaches a target curvature radius in a target direction. After the end of each application of current, the wires remain at a constant length and do not move.

To accommodate the tapered spiral shape of the cochlea, as the cochlear implant is inserted into the ear, the multi-joint robot 800 needs to adjust continuously the angle of the joint actuator units 801. In one embodiment, 10 independent functional segments are included in the multi-joint robot 800 and are controlled by 30 conductive strips 605 in the in the spiral strip cochlear implant 600. For example, one segment can include 10 micro multi-joint actuator units 801 and 30 shape memory alloy wires. In one end of each functional segment, the shape memory alloy wires are connected to conductive strips in the cochlear implant; in the other end of the functional segment the ends of the shape memory alloy wires are connected to the grounded inner tungsten column 804. The multi-joint robot 800 is actuated through feedback control using position sensing to keep the entire cochlear implant-robotic implant device assembly away from the cala tympani wall 701 about a 360 degree field of view along a longitudinal axis of the device.

Figure 9:
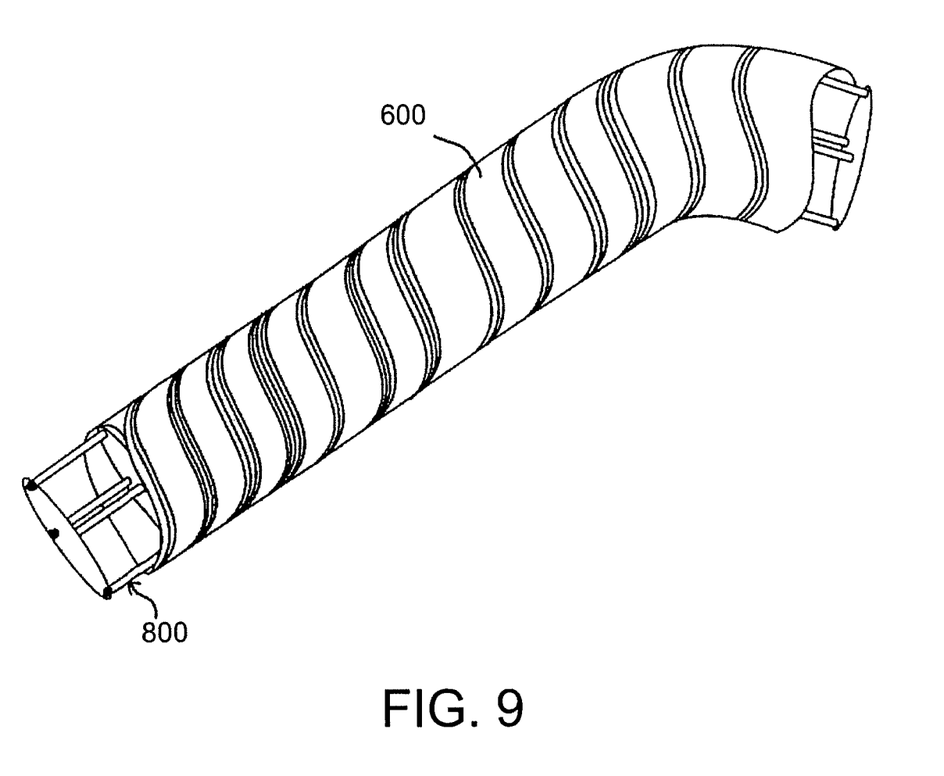
FIG. 9 is a diagrammatic representation of the spiral strip cochlear implant, wrapped around the micro multi-joint actuators.

FIG. 9 illustrates a diagrammatic representation of the spiral strip cochlear implant 600, wrapped around the multi-joint robot 800. As the robotic implant device advances into the scala tympani, it may obtain a, preferably high resolution, scala tympani map of the patient using relative distance information from the multiple sensors and the shape information from the actuators. Using this map, the robotic implant device may calculate the next incremental angle change of the 10 segments independently for the next insertion movement. As the spiral strip cochlear implant 600 is inserted, the sensor and the actuator information may be updated and a new map may be generated. By using this technique, with the cochlear implant wound around the robotic implant device, the system can automatically conform to the shape of the cochlea of each individual patient, thereby placing the cochlear implant within the scala tympani without damage.

Figure 10:
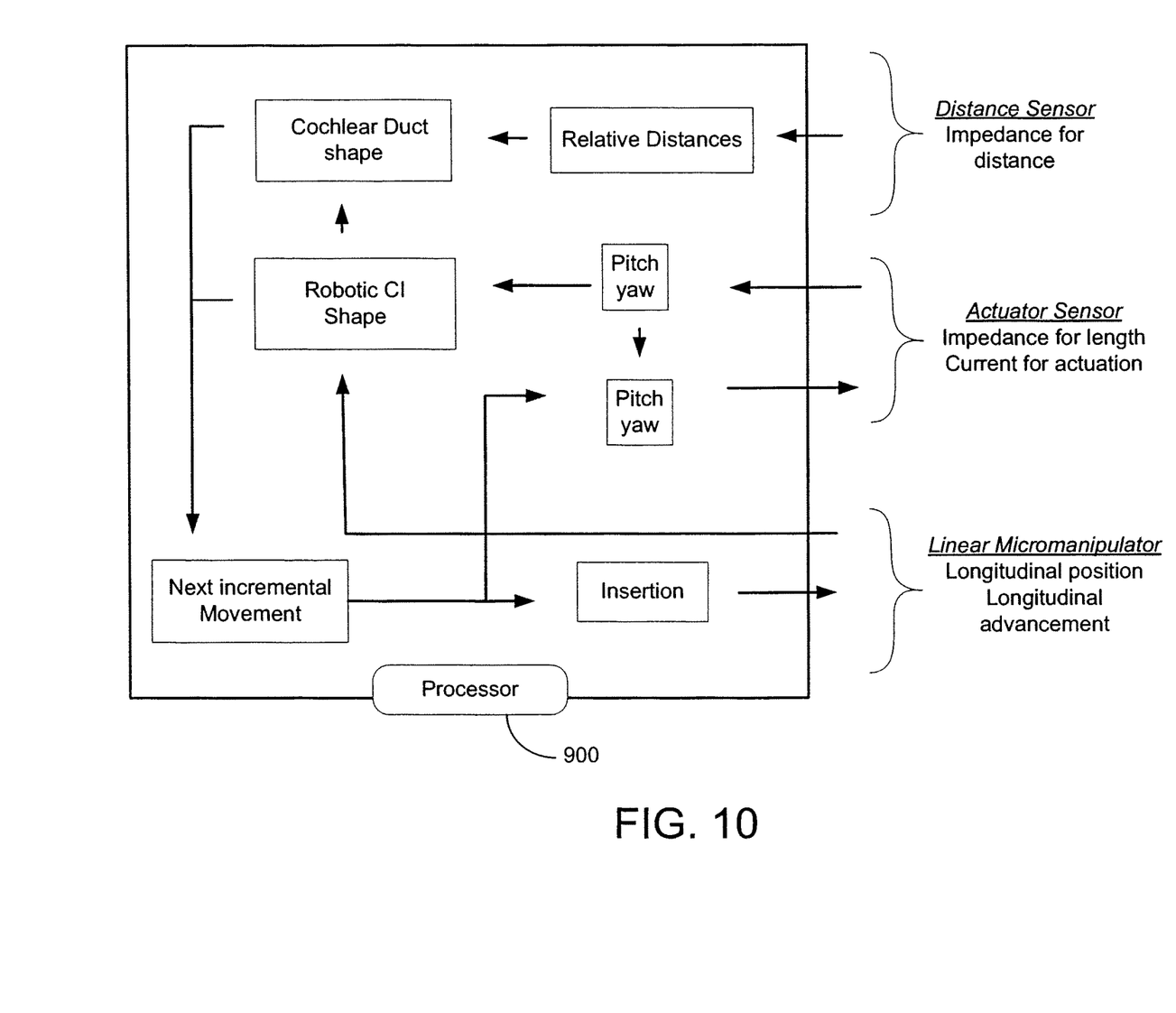
FIG. 10 is a schematic diagram of a control system of the spiral strip cochlear implant using a processor.
Figure 11:
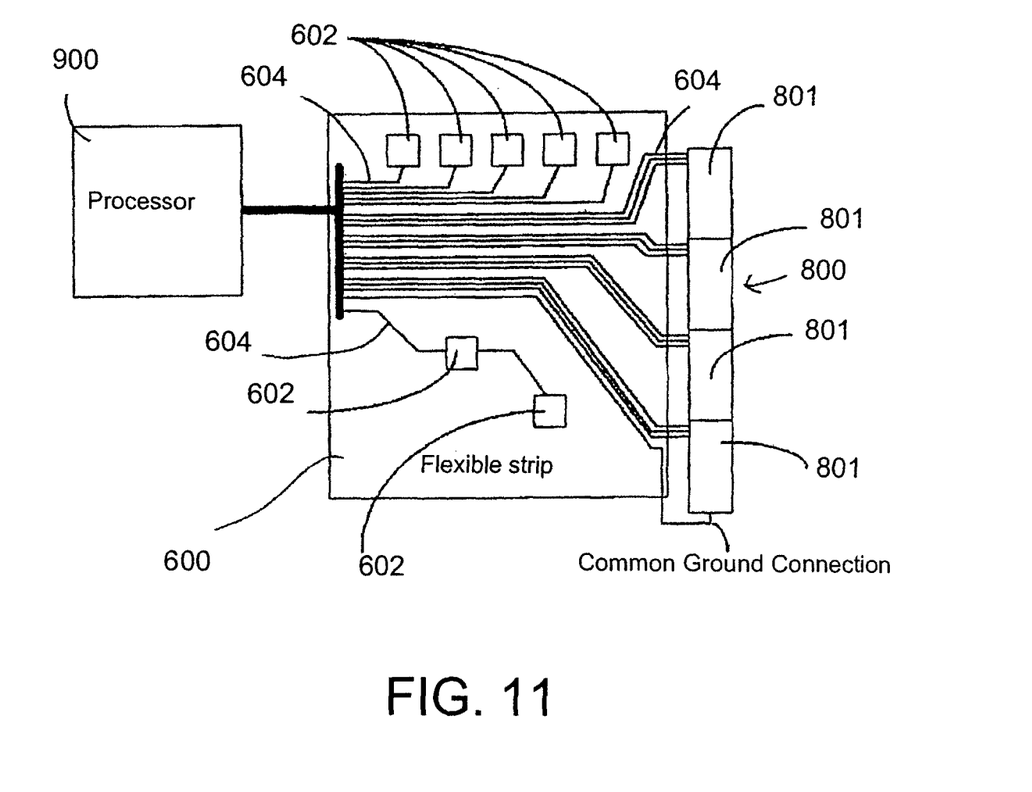
FIG. 11 is a schematic diagram showing the electrical connections between the processor, the spiral strip cochlear implant, and the micro multi-joint actuators of the control system of the spiral strip cochlear implant.

Referring now to FIGS. 10 and 11, FIG. 10 shows a schematic diagram of a control system using a processor 900. FIG. 11 shows a simplified schematic diagram of the electrical connections between the processor 900, the spiral strip cochlear implant 600, and the components of the multi-joint robot 800. The processor 900 may be a traditional microprocessor. Alternatively, the processor 900 may include an application specific integrated circuit (ASIC), a field programmable gate array (FPGA), a complex programmable logic device (CPLD), or a combination of these or other electronic devices.

As illustrated in FIG. 11, the processor 900 is electrically connected to the multi-joint robot 800 through the spiral strip cochlear implant 600. FIG. 11 illustrates dedicated conductive strips 604 that connect the processor 900 to the multi-joint robot 800. Alternatively, conductive strips that are used as electrodes after the spiral strip cochlear implant 600 is inserted may be used to connect the processor to the multi-joint robot 800. After the spiral strip cochlear implant 600 is inserted, the electrical connections to the processor 900 may be removed and replaced, for example, with connections to the receiver 300, preferably through the internal cable 400, During insertion of the spiral strip cochlear implant 600, the processor 900 may monitor and control all of the devices described above. For the distance sensor, the processor 900 may apply triangular voltage between the electrode windows 604 and a reference electrode (e.g. an Ag/AgCl electrode attached to a patient's ear) and may monitor the current passing between the electrodes.

For the micro multi-joint actuator units 801, the processor 900 may cause current to be applied to one or two of the three shape memory alloy wires in each actuator unit 801 in order to heat and thereby contract the wires. The processor 900 may also monitor the required voltage on the wires to calculate impedance at the same time in order to track contraction length. Thus, the processor 900 may adjust the current being applied to the wires in order to precisely control the contraction of the wires. For simplicity, the multi-joint robot 800 is illustrated in FIG. 11 as having only 4 micro multi-joint actuator units 801. However, the multi-joint robot 800 may include in excess of 100 micro multi-joint actuator units 801. Additionally, as described above, the micro multi-joint actuator units 801 may be connected in groups of functional segments that are controlled together. In this case, only three connections, in addition to a common ground connection, would be required between the processor 900 and each functional segment to control multiple multi-joint actuator units 801. Further, although FIG. 11 illustrates a multi-joint robot 800 having a common ground connection shared by all multi-joint actuator units 801, e.g., via an electrical connection between the center columns of the actuator units 801, separate current return paths to the processor 900 for each shape memory alloy wire in the multi-joint robot 800 may instead be included in the spiral strip cochlear implant 600.

For the linear micromanipulator (not shown), the processor 900 may directly control advancement of the cochlear implant and record the longitudinal distance of the robotic cochlear implant in the cochlear duct.

The control system may include a computer-readable storage medium on which is stored one or more sets of instructions (e.g., software code) configured to implement one or more of the methodologies, procedures, or functions described herein. A computer-readable medium containing instructions may also be connected to the processor 900 via external I/O interfaces. The instructions can also reside, completely or at least partially, within the processor 900. The processor 900 may execute the program instructions to perform the functions assigned to the processor 900. Alternatively, the methods, procedures, or functions described herein can be implemented using dedicated hardware implementations. Thus, the exemplary system is applicable to software, firmware, and hardware implementations.

Thus, while there have been shown, described, and pointed out fundamental novel features of the invention as applied to several embodiments, it will be understood that various omissions, substitutions, and changes in the form and details of the illustrated embodiments, and in their operation, may be made by those skilled in the art without departing from the spirit and scope of the invention. Substitutions of elements from one embodiment to another are also fully intended and contemplated.

The invention claimed is:

1. A cochlear implant device, comprising:
a deformable flexible strip including a biological compatible material and having a plurality of conductive strips arranged in a predetermined pattern disposed therein, wherein the deformable flexible strip has inner and outer surfaces;
a plurality of electrode windows formed in at least one of the inner and outer surfaces so as to expose at least one segment in each of the plurality of conductive strips;
the deformable stretchable flexible strip being positioned about a longitudinal axis so as to form a spiral; and
the plurality of electrode windows provided along the deformable stretchable flexible strip configured to monitor a distance of the flexible strip from a nonconductive tissue of a patient at a plurality of locations.

2. The cochlear implant device of claim 1, wherein the plurality of electrode windows is greater than 10 within a 10% longitudinal segment of the spirally formed strip.

3. The cochlera implant device of claim 1, wherein the deformable flexible strip is formed from polydimethylsiloxane.

4. The cochlear implant device of claim 1, wherein the plurality of conductive strips are formed using gold deposition.

5. The cochlear implant device of claim 1, wherein a plurality of electrode windows are formed in at least one of the inner and outer surfaces for each of the plurality of conductive strips.

6. The cochlear implant device of claim 1, wherein a quantity of the plurality of conductive strips is greater than 99.

7. The cochlear implant device of claim 1, wherein the plurality of conductive strips is formed using a photo microlithography process.

8. The cochlear implant device of claim 1, wherein the deformable flexible strip is wrapped to make a helical shape whose pitch angle is 60°.

9. The cochlear implant device of claim 8, wherein the helical shape of the deformable flexible strip includes 40 turns and each turn includes 8 equally-spaced electrode windows.

10. The cochlear implant device of claim 1, wherein the deformable flexible strip forms a spiral by being wrapped around a polyimide tube.

11. The cochlear implant device of claim 1, wherein the plurality of electrode windows provided along the deformable stretchable flexible strip are sufficient to monitor a distance of the flexible strip from a non-conductive tissue of a patient tissue of a patient in a 360degree field of view about the longitudinal axis.

12. The cochlear implant device as defined in claim 1 further including a, multi joint robot comprising:
a plurality of multi joint actuator units interconnected mechanically and controllable electronically;
each of the plurality of multi joint actuator units including at least two central discs, an inner column disposed between the central discs, and at least one wire in communication with the at least two central discs; and
each of the plurality of multi-joint actuator units being capable of independent remote activation by electronic communication.

13. The cochlear implant of claim 12 wherein the actuator units include at least a first actuator unit having an associated wire which contracts when a current is applied to the wire, thereby enabling the wire to adjust one of yaw and pitch of the first actuator unit.

14. The cochlear implant of claim 12, wherein the plurality of multi joint actuator units includes at least ten independent multi joint actuator units.

15. The cochlear implant of claim 12, wherein the wire comprises a plurality of wires distributed at equiangular points along the periphery of the central discs.

16. The cochlear implant of claim 12, wherein the multi joint actuator units are independently activated by selective application of a current to the at least one of the at least three wires, wherein the current causes a tilt in the selected multi-joint actuator unit.

17. The cochlear implant of claim 12, wherein the at least one wire includes nitinol.

18. The cochlear implant of claim 12, wherein the outer surface of the multi-joint robot is configured and arranged to receive a deformable stretchable flexible strip.

19. The cochlear implant device of claim 1 wherein the electrode window provides distance related information and the cochlear implant device further includes a system having a non-transitory computer-readable medium having computer-executable instructions for performing a method comprising the following steps:
receiving the distance related information from a distance sensor associated with the electrode window;
determining a current based at least in part on the distance related information to be applied to a wire associated with a first one of an actuator unit of a multi joint robot so as to contract the wire which is in communication with at least two central disks of the actuator to adjust one of a yaw and a pitch position of the first actuator unit to achieve a target curvature in a target direction;
generating a signal to apply the current to the wire of the actuator unit.

20. The cochlear implant device as defined in claim 19, wherein a plurality of the actuator unit are independently controlled.

21. The cochlear implant device as defined in claim 19, further including a linear micromanipulator which is used to longitudinally advance the multi-joint robot based on a longitudinal position of the multi joint robot.

22. The cochlear implant device as defined in claim 19, wherein the impedance of the wire is used to monitor a contraction length of the wire.

23. A cochlear implant system, comprising:
a microphone operative to acquire and process sound information;
a transmitter, communicatively coupled to the microphone, operative to receive the processed sound information from the microphone and to transmit the processed sound information;
a receiver, operative to receive the transmitted processed sound information from the transmitter, to convert the transmitted processed sound information into electric pulses, and to provide the electric pulses to a cochlear implant;
wherein the cochlear implant is communicatively coupled to the receiver, and wherein the cochlear implant comprises:
a deformable flexible strip including a biological compatible material and having a plurality of conductive strips arranged in a predetermined pattern disposed therein, wherein the deformable flexible strip has inner and outer surfaces;

a plurality of electrode windows formed in at least one of the inner and outer surfaces so as to expose at least one segment in each of the plurality of conductive strips;

the deformable stretchable flexible strip being positioned about a longitudinal axis so as to form a spiral; and the plurality of electrode windows provided along the deformable stretchable flexible strip configured to monitor a distance of the flexible strip from a non-conductive tissue of a patient at a plurality of locations.

24. The cochlear implant system as defined in claim 23 wherein the plurality of electrode windows are formed in at least one of the inner and outer surfaces for each of the plurality of conductive strips.

25. the cochlear implant system as defined in claim 23 wherein the plurality of electrode windows provided along the deformable stretchable flexible strip are sufficient to monitor a distance of the flexible strip from a non-conductive tissue of a patient tissue of a patient in a 360 degree field of view about the longitudinal axis.

26. A method of inserting an implant in a patient, wherein the implant includes a deformable flexible strip including a biological compatible material and having a plurality of conductive strips arranged in a predetermined pattern disposed therein, the method comprising the following steps:

providing a multi joint robot comprised of a series of actuator units;

placing the deformable and stretchable flexible strip about an outer surface of the multi-joint robot;

guiding the multi-joint robot into the patient;

monitoring a position of the multi-joint robot relative to a non-conductive portion of the patient; and applying current to the multi joint robot so as to adjust one of the yaw and pitch position of one or more of the actuator units.

27. The method of claim 26, wherein the monitoring step includes using scanning electrochemical microscopy.

28. The method of claim 27, wherein using the scanning electrochemical microscopy includes using scanning electrochemical microscopy in negative mode.

29. The method of claim 27, wherein the implant includes exposed electrode windows, each of which are of a suitable size to be detected by the scanning electrochemical microscopy so as to indicate a positional separation from the non-conductive portion.

* * * * *